United States Patent
LaPlaca et al.

(10) Patent No.: US 8,568,311 B2
(45) Date of Patent: Oct. 29, 2013

(54) DISPLAY ENHANCED TESTING FOR CONCUSSIONS AND MILD TRAUMATIC BRAIN INJURY

(75) Inventors: Michelle C. LaPlaca, Atlanta, GA (US); David W. Wright, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 1300 days.

(21) Appl. No.: 11/503,579

(22) Filed: Aug. 10, 2006

(65) Prior Publication Data

US 2007/0027406 A1    Feb. 1, 2007

Related U.S. Application Data

(63) Continuation of application No. PCT/US2005/004515, filed on Feb. 11, 2005.

(60) Provisional application No. 60/544,465, filed on Feb. 13, 2004.

(51) Int. Cl.
  *G09B 19/00*    (2006.01)
  *A61B 5/16*    (2006.01)
  *G06Q 50/22*    (2012.01)

(52) U.S. Cl.
  USPC ........... 600/301; 600/300; 434/236; 434/238; 128/920

(58) Field of Classification Search
  None
  See application file for complete search history.

(56) References Cited

U.S. PATENT DOCUMENTS

| 4,770,636 | A |   | 9/1988  | Buschke |   |
|-----------|---|---|---------|---------|---|
| 5,230,629 | A |   | 7/1993  | Buschke |   |
| 5,678,571 | A |   | 10/1997 | Brown   |   |
| 6,012,926 | A | * | 1/2000  | Hodges et al. | 434/236 |
| 6,046,712 | A | * | 4/2000  | Beller et al. | 345/8 |
| 6,149,586 | A | * | 11/2000 | Elkind | 600/300 |
| 6,305,942 | B1 | * | 10/2001 | Block et al. | 434/156 |
| 6,425,764 | B1 | * | 7/2002  | Lamson | 434/236 |
| 6,503,085 | B1 | * | 1/2003  | Elkind | 434/236 |
| 6,602,202 | B2 | * | 8/2003  | John et al. | 600/559 |
| 6,669,481 | B2 | * | 12/2003 | Winter et al. | 434/236 |
| 6,896,655 | B2 | * | 5/2005  | Patton et al. | 600/300 |
| 6,964,638 | B2 | * | 11/2005 | Theodoracopulos et al. | 600/300 |
| 7,087,015 | B1 | * | 8/2006  | Comrie et al. | 600/300 |
| 7,207,804 | B2 | * | 4/2007  | Hersh | 434/236 |
| 8,062,129 | B2 | * | 11/2011 | Pope et al. | 463/31 |
| 2004/0229198 | A1 | * | 11/2004 | Boyd et al. | 434/236 |
| 2005/0165327 | A1 | * | 7/2005  | Thibault et al. | 600/558 |

OTHER PUBLICATIONS

Sony GlasstronTM model PLM-A55: http://www.mindflux.com.au/products/sony/plm-a55.html, accessed on Apr. 16, 2012.*

(Continued)

*Primary Examiner* — Bill Thomson
*Assistant Examiner* — Shirley Jian
(74) *Attorney, Agent, or Firm* — Emory Patent Group; Randi Beth Isaacs

(57) ABSTRACT

Cognitive assessment systems and methods that provide an integrated solution for evaluating the presence or absence of cognitive impairment. The present invention is used to test cognitive functions of an individual including information processing speed, working memory, work list learning and recall, along with variations of these tasks. Immersive and non-immersive systems and methods are disclosed. Testing and results feedback using the present invention may be completed in real time, typically in less than 15 minutes.

37 Claims, 5 Drawing Sheets

(56) References Cited

OTHER PUBLICATIONS

Rose, F.D. et al., "Virtual Environments in Neuropsychological Assessment and Rehabilitation," *Virtual Reality in Neuro-Psycho-Physiology*, 1997, 1998, pp. 1-9.

Riva, G., "Virtual Reality in Neuroscience: A Survey," *Virtual Environments in Clinical Psychology and Neuroscience*, 1998, pp. 1-9.

Rizzo, A. et al., "Virtual Reality and Cognitive Assessment and Rehabilitation: The State of the Art," *Virtual Reality in Neuro-Psycho-Physiology*, 1997, 1998, pp. 1-26.

Gualieri, et al., Neurocognitive Testing Supports a Broader Concept of Mild Cognitive Impairment, American Journal of Alzheimer's disease and Other Dementias, vol. 20, No. 6, Nov./Dec. 2005, pp. 359-366.

Gualtier, et al., Psychometric and Clinical Properties of a New Computerized Neurocogntive Assessment, Feb. 24, 2004, American Neuropsychiatric Associa. Annual Meeting, Bal Harbor, FL.

Gualtieri, et al., A Computerized Test Battery Sensitive to Mild and Severe Brain Injury, Medscape J Med. 2008: 10(4).

Gualtieri, et al., Reliability and Validity of a Computerized Neurocognitive Test Battery, CNS Vital Signs, Archives of Clinical Neuropsychology 21 (2006) 623-643.

Heyn et al., Computerized Cognitive Test Performance in Computer User and Non-User Older Adults.

Hinton-Bayre, et al., Concussion in Contact Sports: Reliable Change Indices of Impairment and Recovery, Journal of Clinical and Experimental Neuropsychology, 1999, vol. 21, No. 1, pp. 70-86.

Hobart, et al. Repeatable Battery for the Assessment of Neuropsychological Status as a Screening Test in Schizophrenia, II: Convergent/Discriminate Validity and Diagnostic Group Comparisons, Am J Psychiatry 156:12, Dec. 1999, pp. 1951-1957.

http://cogstate.com/go/corporate/about, CogState Limited, Oct. 22, 2008, pp. 1-2.

https://www.cnsys.com/index.php?option+com_content&task-view, CNS Vital Signs—Advancing Neurocognitive Care, CNS Vital Signs—Clinical Trials, Oct. 22, 2008, pp. 1-4.

Hugenholtz et al., How Long Does it Take to Recover From Mild Concussion?, Neurosurgery, 1988, pp. 853-858, 22.

Jorge et al., Comparison Between Acute-and Delayed-Inset Depression Following Traumatic Brain Injury, J Neuropsychiatry Clin Neurosci., 1993, pp. 43-49, 5 (1).

Kelly et al., Concussion in Sports, Guidelines for the Prevention of Catastrophic Outcome, JAMA, 1991, pp. 2867-2869, 266(20).

Killam, et al., Assessing the Enduring Residual Neuropsychological Effects of Head Trauma in College Athletes Who Participate in Contact Sports, Archives of Clinical Neuropsychology 20 (2005) 599-611.

Larson EB, et al., Construct and Predictive Validity of the Repeatable Battery for the Assessment of Neuropsychological Status in the Evaluation of Stroke Patients, Web of Science, ISI Web of knowledge (v. 4.4), (Nov. 15, 2008), pp. 1-2.

Leininger et al., Neuropsychological Deficits in Symptomatic Minor Head Injury Patients After Concussion and Mild Concussion, J Neurol Neurosurg Psychiatry, 1990, pp. 293-296, 53(4).

Leitner, et al., A Novel Multi-domain Computerized Cognitive Assessment for Attention-Deficit Hyperactivity Disorder: Evidence for Widespread and Circumscribed Cognitive Deficits, Journal of Child Neurology vol. 22, No. 3, Mar. 2007, 264-276, 2007 Sage Publication.

Levin et al., Depression as a Secondary Condition Following Mild and Moderate Traumatic Brain Injury, Seminars in Clinical Neuropsychiatry, 1997, pp. 207-215 (2).

Levin et al., Neurobehavioral Outcome Following Minor Head Injury: A Three-Center Study, J Neurosurg, 1987, pp. 234-243, 66(2).

Levin et al., The Neurobehavioural Rating Scale: Assessment of the Behavioural Sequelae of Head Injury by the Clinician, Journal of Neurology, Neurosurgery & Psychiatry, 1987, pp. 183-193, 50(2).

Lighthall et al., Toward a Biomechanical Criterion for Functional Brain Injury, Society of Automotive Engineers, Inc., 1989.

MacAulay, et al., Geriatric Performance on the Neurobehavioral Cognitive Status Examination (Cognistat) What is normal? Archives of Clinical Neuropsychology 18 (2003) 463-471.

Macciocchi et al., Neuropsychological Functioning and Recovery After Mild Head Injury in Collegiate Athletes, Neurosurgical Psychiatry, 1984, p. 510-4, 39(3).

MacFlynn et al., Measurement of Reaction Time Following Minor Head Injury, Journal of Neurology and Neurosurgical Psychiatry, 1984.

Margulies et al., A Proposed Tolerance Criterion for Diffuse Axonal Injury in Man, Journal of Biomechanics, 1992, pp. 917-923, 25(8).

Mathias, et al., Emotional and Cognitive Sequelae to Mild Traumatic Brain Injury, Journal of Clinical and Experimental Neuropsychology, 1999, vol. 21, No. 2, pp. 200-215.

Mayeux et al., Genetic Susceptibility and Head Injury as Risk Factors for Alzheimer's Disease Among Community-Dwelling Elderly Persons and Their First-Degree Relatives, Ann Neurol, 1993, pp. 494-501, 33.

McKay C, et al., The Repeatable Battery for the Assessment of Neuropsychological Status (rbans): Clinical Utility in a Traumatic Brain Injury Sample, ISI Web of Knowledge [v.4.]—Web of Science.

McKay, et al., Reliability and Validity of the RBANS in a Traumatic Brain Injured Sample, Archives of Clinical Neuropsychology 22 (2007) 91-98.

McNeil, Alzheimer's disease: Unraveling the Mystery, NIB, National Institute on Aging, Bethesda, MD, 1997

Melton, Psychometric Evaluation of the Mindstreams Neuropsychological Screening Tool, Navy Experimental Diving Unit, Jun. 2005, pp. 1-19.

Mittenberg, et al., Cognitive-Behavioral Prevention of Postconcussion Syndrome, Archives of Clinical Neuropsychology, vol. 11, No. 2, pp. 139-145, 1996.

Nemetz, et al., Traumatic Brain Injury and Time on Onset of Alzheimer's Disease: A Population-Based Study, vol. 149(1), Jan. 1, 1999, pp. 32-40.

NeuroTrax, www.neurotrax.com; pp. 1-2.

Pietrzak, et al., An Examination of the Construct Validity and Factor Structure of the Groton Maze Learning Test, a New Measure of Spatial Working Memory, Learning Efficiency, and Error Monitoring, Archives of Clinical Neuropsychology 23 (2008) 433-445.

Ponsford et al., Factors Influencing Outcome Following Mild Traumatic Brain Injury in Adults, Journal of the International Neuropsychological Society, 2000, pp. 568-579, 6(5).

Pottie CG, et al., Education, Age, and Laterality Effects on RBANS Performance in Stroke, Web of Science, ISI Web of knowledge (v. 4.4), pp. 1-2.

Randolph, et al., The Repeatable Battery for the Assessment of Neuropsychological Status (RBANS): Preliminary Clinical Validity, Journal of Clinical and Experimental Neuropsychology, 1998, vol. 20, No. 3, pp. 310-319.

Ritsner, et al., The Detection of Neurocognitive Decline in Schizophrenia Using the Mindstreams Computerized Cognitive Test Battery, Schizophrenia Research, Elsevier 2005.

Riva, Psychotherapy: Theory, Research, Practice, Training, American Psychological Association, vol. 40(1-2), Spring/Summer 2003, pp. 68-76, Ios Press: Amsterdam, Netherlands.

Riva, Virtual Reality in Neuroscience: A Survey, Virtual Environments in Clinical Psychology and Neuroscience 1998, Ios Press: Amsterdam, Netherlands.

Rizzo, et al., Virtual Reality and Cognitive Assessment and Rehabilitation: The State of the Art, Virtual Reality in Neuro-Psycho-Physiology, 1997, 1998, 26 pages, Ios Press: Amsterdam, Netherlands.

Rose, et al., Virtual Environments in Neuropsychological Assessment and Rehabilitation, Virtual Reality in Neuro-Psycho-Physiology, 9 pages, Ios Press: Amsterdam, Netherlands.

Rutherford, et al., Symptoms at One Year Following Concussion From Minor Head Injuries, Injury, 1979, 10(3), pp. 225-230.

Schoenberg, et al., Retention Rates of RBANS Memory Subtests in Elderly Adults, Journal of Geriatric Psychiatry and Neurology, vol. No. 21, Mar. 2008 pp. 26-33.

Schoschoenhuber et al., Anxiety and Depression after Mild Head Injury: A Case Control Study, Journal of Neurology, Neurosurgery & Psychiatry, 1988, pp. 722-724, 51 (5).

(56) References Cited

OTHER PUBLICATIONS

Schrimsher, et al., The Relation Between Ethnicity and Cognistat Performance in Males Seeking Substance Use Disorder Treatment, Journal of Clinical and Experimental Neuropsychology, 27:873-885, 2005.
Schweiger, et al., Reliability of a Novel Computerized Neuropsychological Battery for Mild Cognitive Impairment, ACTA Neuropsychological, pp. 407-413.
Stambrook et al., Effects of Mild, Moderate and Severe Closed Head Injury on Long-Term Vocational Status, Brain Injury, 1990, pp. 183-190, 4 (2).
The Science of CogState, http://cogstate.com/html/diagnosticdivision.html, Oct. 29, 2003.
Thurman, et al., Trends in Hospitalization Associated With Traumatic Brain Injury, American Medical Association, vol. 282(10), Sep. 8, 1999, pp. 954-957.
Agner, et al., Neurocognitive Assessment Before and After Cranioplasty, Acta Neurochir (2002) 144: 1033-1040.
Anonymous, Injury Fact Book, 2002, National Center for Injury Prevention and Control, Atlanta.
Beatty, et al., Analyzing the Subcortical Dementia Syndrome of Parkinson's Disease Using the RBANS, Archives of Clinical Neuropsychology 18 (2003) 509-520.
Beatty, et al., RBANS Performance: Influences of Sex and Education, Journal of Clinical and Experimental Neuropsychology 2003, vol. 25, No. 8. pp. 1065-1069.
Buschke et al., Evaluating Storage, Retention, and Retrieval in Disordered Memory and Learning, Neurology, 1974, pp. 1019-1025, 24(11).
Cantab Expedio, A New Development in Cognitive Assessment; pp. 1-2.
CANTAB: CANTAB Tests—Overview Neuropsychological Tests From Cambridge Cognition, http://camcog.com/science/cantab-tests-all.asp, Oct. 22, 2008.
Cantu et al., Catastrophic Football Injuries: 1977-1998, Neurosurgery, 2000, pp. 673-675; discussion 675-747, 3.
Cantu, et al., Second Impact Syndrome—A Risk in Any Contact Sport, Physician and Sports Medicine, Jun. 1995, Case Report; vol. 23, No. 6; p. 27.
Cantu, Head and Spine Injuries in Youth Sports, Clinics in Sports Medicine, 1995, pp. 517-532, 14(3). (abstract only, full document available on request).
Cantu, Head Injuries in Sport, British Journal of Sports Medicine, 1996, pp. 289-296, 30(4).
Cantu, Neurologic Athletic Head and Neck Injuries, Second-Impact Syndrome, Clinics in Sports Medicine, vol. 17, No. 1, Jan. 1998, pp. 37-44.
Cantu, Reflections on Head Injuries in Sport and the Concussion Controversy, Clinical Journal of Sport Medicine, 1997, pp. 83-84, 7(2). (abstract only, full document available on request).
Collie, et al., Psychometric Issues Associated With Computerized Neuropsychological Assessment of Concussed Athletes, Br. J. Sports Med. 2003:37; 556-559.
Commerce, U.S.D.o., Statistical Abstract of the United States 1997. 1997 U.S. Department of Commerce, Bureau of the Census.
Darby, et al., Mild Cognitive Impairment Can Be Detected by Multiple Assessments in a Single Day, AAN Enterprises, Inc., Neurology 2002; 59: 1042-1046.
Dickerson, et al., Cognitive Functioning in Schizophrenia and Bipolar Disorder: Comparison of Performance on the Repeatable Battery for the Assessment of Neuropsychological Status, Psychiatry Research 129 (2004) 45-53.
Dikmen et al., Neurobehavioral Outcomes and Their Determinants, Journal of Head Trauma Rehabilitation, 1995, pp. 74-86, 10(1).
Dikmen et al., Neuropsychological and Psychosocial consequences of Minor Head Injury, J Neurol Neurosurg Psychiatry, 1986, pp. 1227-1232, 49 (11).

Doniger GM, et al., Towards Practical Cognitive Assessment for Detection of Early Dementia: a 30-Minute Computerized Battery Discriminates as Well as Longer Testing, BenthamDirect, Sep. 19, 2008, pp. 1-2.
Drane, et al., Healthy Older Adult Performance on a Modified Version of the Cognistat (NCSE): Demographic Issues and Preliminary Normative Data, Journal of Clinical and Experimental Neuropsychology, 2003, vol. 25, No. 1, pp. 133-144.
Duff, et al. Normative and Retest Data on the RBANS Cortical/Subcortical Index in Older Adults, ISI Web of Knowledge [v.4.4]—Web of Science, pp. 1-2.
Duff, et al., Age- and Education-corrected Independent Normative Data for the RBANS in a Community Dwelling Elderly Sample, Clinical Neuropsychologist, vol. 17, Aug. 2003, pp. 351-366.
Duff, et al., Examining the Repeatable Battery for the Assessment of Neuropsychological Status: Factor Analytic Studies in an Elderly Sample, AmJ Geriat Psychiatry 14:11, Nov. 2006, pp. 976-979.
Duff, et al., Modified Scoring Criteria for the RBANS Figures, Applied Neuropsychology, vol. 14, Issue 2, pp. 73-83, Web of Science, ISI Web Knowledge (v. 4.4).
Duff, et al., Predicting Change With the RBANS in a Community Dwelling Elderly Sample, ISI Web of Knowledge [v.4.4]—Web of Science, pp. 1-2.
Duff, et al., Predicting Cognitive Change Across 3 Years in Community-Dwelling Elders, ISI Web Knowledge [v.4.4]—Web of Science, pp. 1-2.
Duff, et al., Regression-Based Formulas for Predicting Change in RBANS Subtests With Older Adults, Archives of Clinical Neuropsychology 20 (2005) 281-290.
Duff, et al., Test-Retest Stability and Practice Effects of the RBANS in a Community Dwelling Elderly Sample, Journal of Clinical and Experimental Neuropsychology, 27:565-575, 2005.
Duff, et al., Test-Retest Stability and Practice Effects of the RBANS in a Community Battery.
Duff, et al., Utility of the RBANS in Detecting Cognitive Impairment Associated With Alzheimer's Disease: Sensitivity, Specificity, and Positive and Negative Predictive Powers, Archives of Clinical Neuropsychology 23 (2008) 603-612.
Egerhazi, et al., Automated Neuropsychological Test Batter (CANTAB) in Mild Cognitive Impairment and in Alzheimer's Disease, Elseiver, 2007, pp. 746-751.
Eisenstein, et al., Normative Data for Healthy Elderly Persons With the Neurobehavioral Cognitive Status Exam (Cognistat), Applied Neuropsychology, 2002, vol. 9, No. 2, 110-113.
Engelhart, et al., Factor Structure of the Neurobehavioral Cognitive Status Exam (COGNISTAT) in Healthy, and Psychiatrically and Neurologically Impaired, Elderly Adults, The Clinical Neuropsychologist, 1999, vol. 13, No. 1, pp. 109-111.
Englander et al., Mild Traumatic Brain Injury in an Insured Population: Subjective Complaints and Return to Employment, Brain Tnj., 1992, pp. 161-166, 6(2).
Erlanger, et al., Neuropsychology of Sports-Related Head injury: Dementia Pugilistica to Post Concussion Syndrome, The Clinical Neuropsychologist, 1999, vol. 13, No. 2, pp. 193-209.
Evans et al., Prevalence of Alzheimer's disease in a Community Population of Older Persons. Higher Than Previously Reported, JAMA, 1989, pp. 2551-2556. 262(18).
Fann, et al., Psychiatric Disorder and Functional Disability in Outpatients With Traumatic Brain Injuries, The American Journal of Psychiatry; Oct. 1995; 152, 10; Research Library, pp. 1493-1499.
Farm et al., Psychiatric Disorders and Functional Disability in Outpatients with Traumatic Brain Injuries, Am J Psychiatry, 1995, pp. 1493-1499, 152 (10).
Fenton et al., The Postconcussional Syndrome: Social Antecedents and Psychological Sequelae, British Journal of Psychiatry, 1993, pp. 493-497, 162.
Fleminger, et al., Head Injury as a Risk Factor for Alzheimer's Disease: the Evidence 10 Years on; a Partial Replication, J. Neurol. Neurosurg, Psychiatry 2003; 73; 857-862.
Frankowski et al., Part 1: The Descriptive Epidemiology of Head Trauma in the United States, Central Nervous System Trauma Status Report, 1985.

(56) References Cited

OTHER PUBLICATIONS

Garcia, et al., Component Structure of the Repeatable Battery for the Assessment of Neuropsychological Status in Dementia, Archives of Clinical Neuropsychology, 23 (2008) 63-72.
Gold, et al. Repeatable Battery for the Assessment of Neuropsychological Status as a Screening Test in Schizophrenia, I: Sensitivity, Reliability, and Validity, Am J Psychiatry 156:12, Dec. 1999, pp. 1944-1950.
Gomez-Hernandez, et al., Social Impairment and Depression After Traumatic Brain Injury, Arch Phys Med Rehabil vol. 78, Dec. 1997, pp. 1321-1326.
Graham et al., Distribution of Beta-Amyloid Protein in the Brain Following Severe Head Injury, Neuropathol Appl Neurobiol, 1995, pp. 27-34, 21. (abstract only, full document available on request).
Gronwall et al., Delayed Recovery of Intellectual Function After Minor Head Injury, Lancet, 1974, pp. 605-609, 2 (7881).
Gronwall et al., Memory and Information Processing Capacity After Closed Head Injury, J Neurosurg Psychiatry, 1981, pp. 889-895, 44 (10).
Gronwall, Cumulative and Persisting Effects of Concussion on Attention and Cognition, Mild Head Injury, 1989, pp. 153-162, Oxford University Press, New York.
Gronwall, Performance Changes During Recovery from Closed Head Injury, Proc Aust Assoc Neurol. 1976, pp. 143-147, 13.
Van Der Naalt, et al., One Year Outcome in Mild to Moderate Head Injury: The Predictive Value of Acute Injury Characteristics Related to Complaints and Return to Work, J. Neurol. Neurosurg. Psychiatry 1999;66;207-213.
Van Der Naalt, Prediction of Outcome in Mild to Moderate Head Injury: A Review, Journal of Clinical and Experimental Neuropsychology 2001, vol. 23, No. 6, pp. 837-851.
Website www.brainsource.com.
Westerman, et al., Computer-Assisted Cognitive Function Assessment of Pilots, ADF Health vol. 2 Apr. 2001; 2: 29-36.
Wilk, et al., Brief Cognitive Assessment in Schizophrenia: Normative Data for the Repeatable Battery for the Assessment of Neuropsychological Status, Schizophrenia Research 70 (2004) 175-186.
Wilk, et al., Test-Retest Stability of the Repeatable Battery for the Assessment of Neuropsychological Status in Schizophrenia, Am J Psychiatry 159:5, May 2002.
Barker et al., The Detect™ System: portable, reduced-length neuropsychological testing for mild traumatic brain injury via a novel immersive environment, Journal of Medical Engineering & Technology, 2007, pp. 161-169.
(Author Unknown), Sports-Related Recurrent Brain Injuries—United States, JAMA, Apr. 16, 1997, pp. 1190-1191, vol. 277, No. 15, CDC.
(Author Unknown), Report to Congress on Mild Traumatic Brain Injury in the United States: Steps to Prevent a Serious Public Health Problem, CDC, Sep. 2003.
(Author Unknown), Traumatic Brain Injury—Fact Sheet, CDC Injury Prevention, 8 pages.
Gronwall et al., Cumulative Effect of Concussion, The Lancet, Nov. 22, 1975, pp. 995-997.
Collins et al., Relationship Between Concussion and Neuropsychological Performance in College Football Players, JAMA, Sep. 8, 1999, vol. 282, No. 10, pp. 964-970.
Kelly, Traumatic Brain Injury and Concussion in Sports, JAMA, Sep. 8, 1999, vol. 282, No. 10, pp. 989-991.
Wright et al., Use of a novel technology for presenting screening measures to detect mild cognitive impairment in elderly patients, Blackwell Publishing Ltd., The International Journal of Clinical Practice, 2010, pp. 1-8.

\* cited by examiner

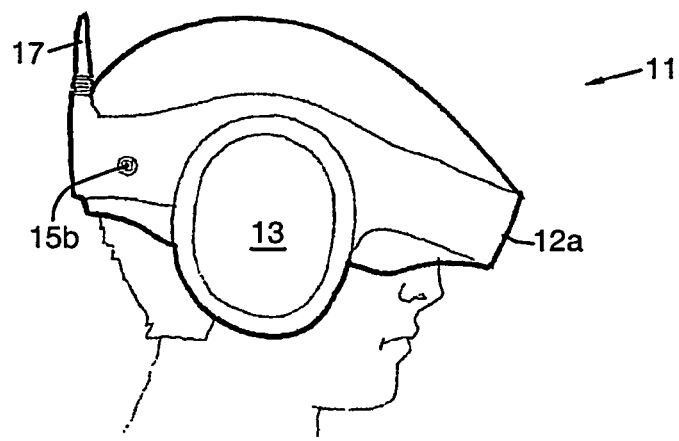
Fig. 4
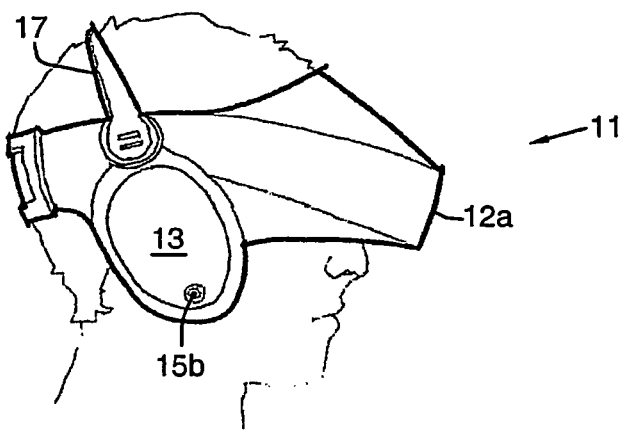
Fig. 5
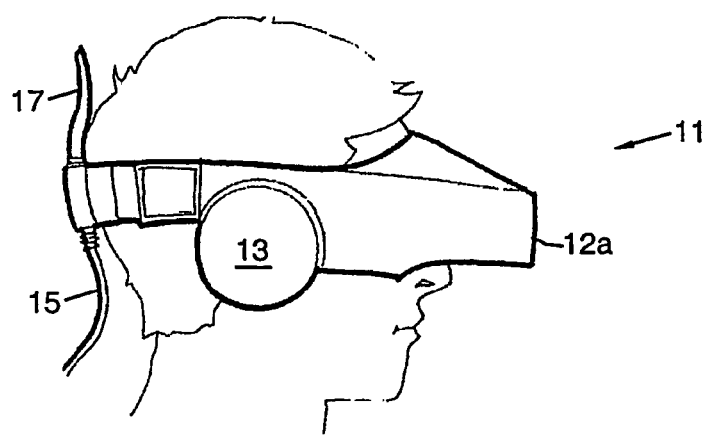
Fig. 6
Fig. 8
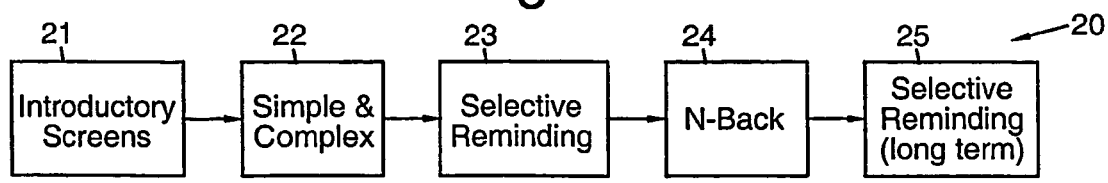

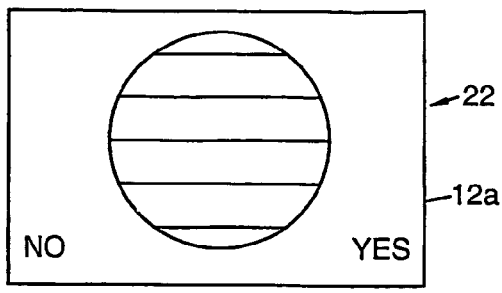
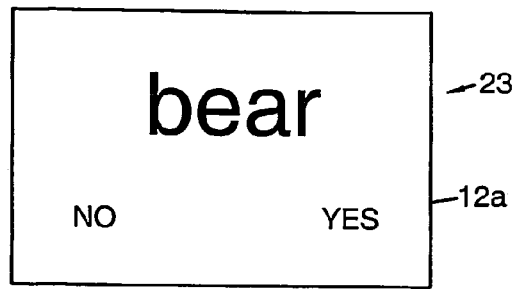
Fig. 9    Fig. 10
Fig. 11
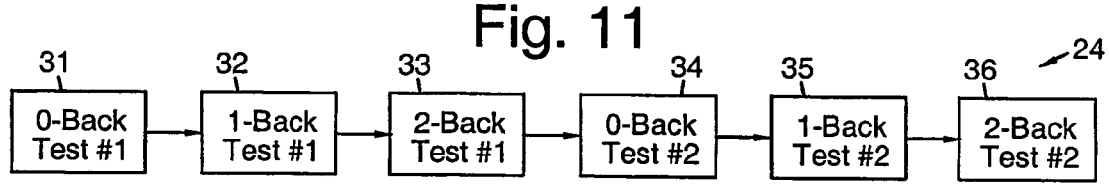
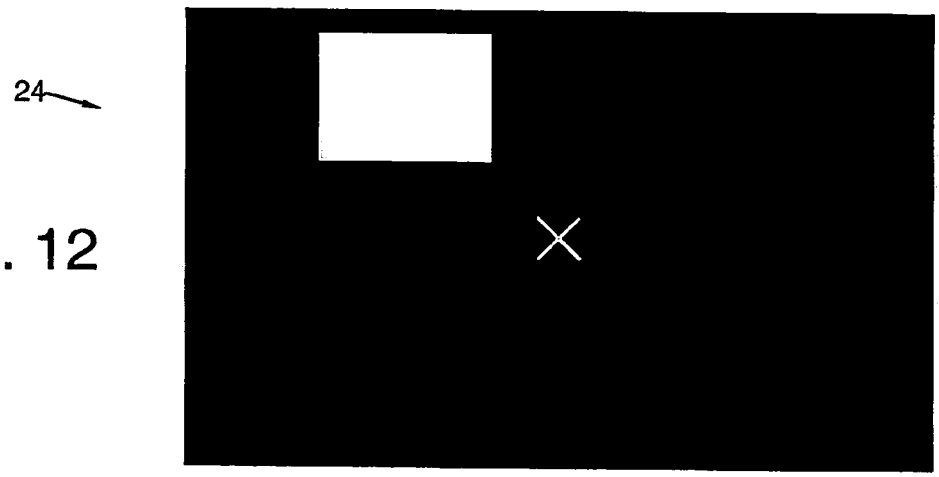
Fig. 12
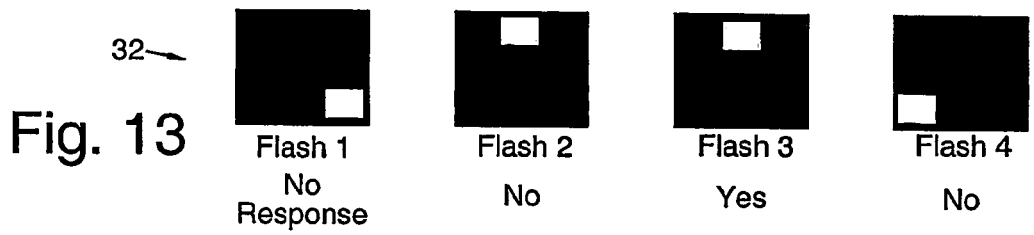
Fig. 13
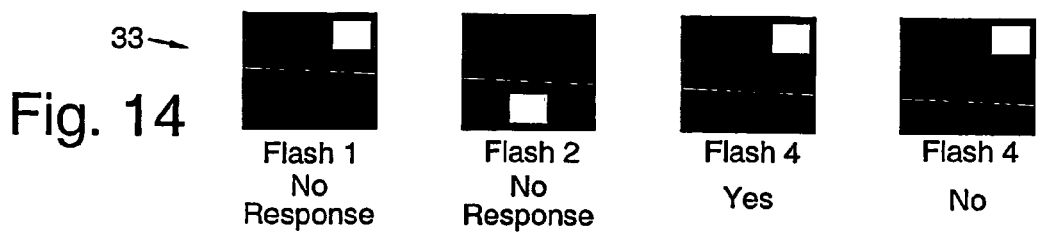
Fig. 14

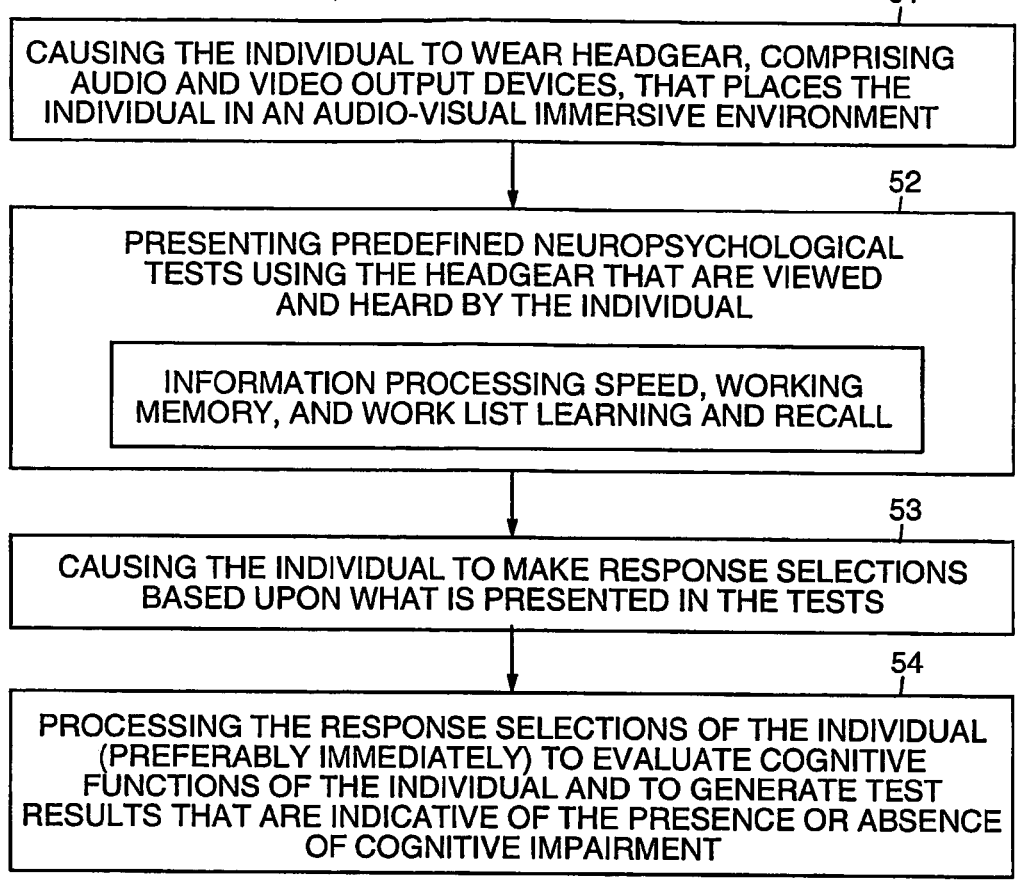
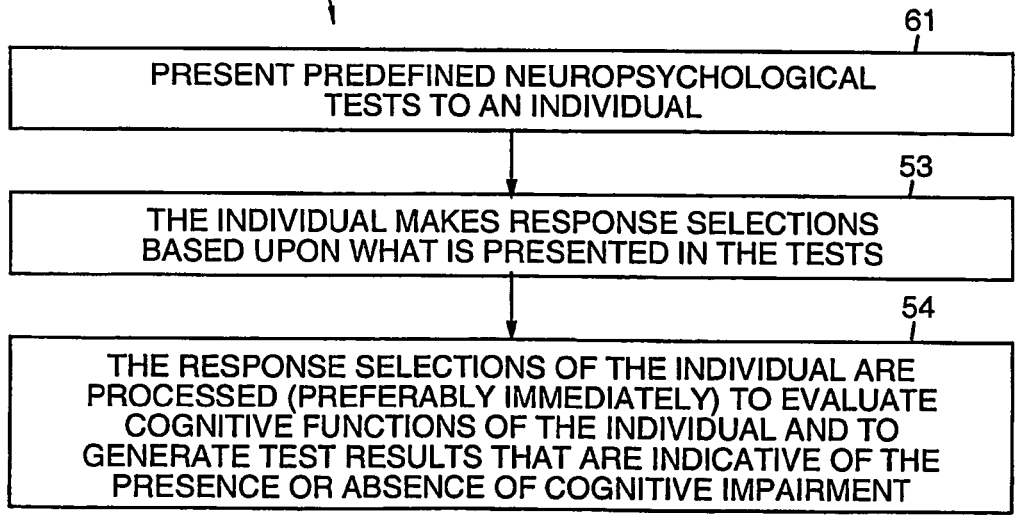

DISPLAY ENHANCED TESTING FOR CONCUSSIONS AND MILD TRAUMATIC BRAIN INJURY

CROSS REFERENCE TO RELATED APPLICATIONS

This application is a continuation application under 1.53(b) of International Application No. PCT/US2005/004515, filed on Feb. 11, 2005, which claims the benefit of priority U.S. Provisional Application No. 60/544,465 filed on Feb. 13, 2004, which applications are hereby incorporated by this reference in their entireties.

TECHNICAL FIELD

The present invention relates generally to an assessment tool for diagnosing cognitive injuries and impairments, in an audio-visually immersive environment.

BACKGROUND

Mild traumatic brain injury (mTBI), commonly known as concussion, describes an insult to the head that, in turn, causes an injury to the brain. It most often occurs from direct contact to the head, but can also result from indirect injury (e.g., whiplash injury or violent shaking of the head). Individuals who have suffered one brain injury are three times more at risk for a second brain injury and eight times more susceptible for subsequent injuries (see the website www.brainsource.com). Regardless of the severity, the second injury to the brain can be life-threatening if incurred within a short time interval (see Cantu, R. C. and F. O. Mueller, *Catastrophic football injuries: 1977-1998*, Neurosurgery, 2000, 47(3): p. 673-5; discussion 675-7, and Kelly, J. P., et al., *Concussion in sports, Guidelines for the prevention of catastrophic outcome*, JAMA, 1991.266(20): p. 2867-9). Also, the damage from successive concussions is cumulative (see Cantu, R. C., *Second-impact syndrome*, Clinics in Sports Medicine, 17(1): 37-44, 1998, and the Catastrophic football injuries paper cited above).

Functions commonly affected by mTBI are cognition, movement, sensation, and emotion (see Table 1, and Mathias, J. L. and J. L. Coats, *Emotional and cognitive sequelae to mild traumatic brain injury*, Journal of Clinical & Experimental Neuropsychology, 1999, 21(2): p. 200-15, Schoenhuber, R. and M. Gentilini, *Anxiety and depression after mild head injury: a case control study*, Journal of Neurology, Neurosurgery & Psychiatry, 1988. 51(5): p. 7224, and Rutherford, W. H., J. D. Merrett, and J. R. McDonald, *Symptoms at one year following concussion from minor head injuries*, Injury, 1979. 10(3): p. 225-30).

Additional risks from a series of concussions include premature senility and Alzheimer's disease (see Fleminger S, Oliver D L, Lovestone S, Rabe-Hesketh S, Giora A., *Head injury as a risk factor for Alzheimer's disease: the evidence 10 years on; a partial replication*, J Neurol Neurosurg Psychiatry, 2003 July; 74(7):841, Mayeux, R., Ottman, R., Tang, M. X., Noboa-Bauza, L., Marder, K., Gurland, B., and Stern, Y. 1993. *Genetic susceptibility and head injury as risk factors for Alzheimer's disease among community-dwelling elderly persons and their first-degree relatives*, Ann Neurol 33: 494-501, Graham, D. I., Gentleman, S. M., Lynch, A., and Roberts, G. W. 1995, *Distribution of beta-amyloid protein in the brain following severe head injury*, Neuropathol Appl Neurobiol 21: 27-34, and Nemetz, P. N., Leibson, C., Naessens, J. M., Beard, M., Kokmen, E., Annegers, J. F., and Kurland, L. T. 1999, *Traumatic brain injury and time to onset of Alzheimer's disease: a population-based study*, American Journal of Epidemiology 149: 32-40.

TABLE 1

| Overview of areas impacted by mTBI | |
|---|---|
| Cognition | Concentration memory, judgment mood |
| Movement | Strength coordination balance |
| Sensation | Tactile and special senses (vision) |
| Emotion | Instability, impulsivity |

Traumatic brain injuries (TBI) are often classified into mild, moderate and severe TBI based on three parameters: 1) the quality and length of change in consciousness, 2) the length of amnesia (memory loss), and 3) the Glasgow Coma Scale (GCS) (Table 2).

TABLE 2

| TBI classification criteria | | | |
|---|---|---|---|
| TBI Classification | Length of Loss of Consciousness | Length of Amnesia | Glasgow Coma Scale Score |
| Mild TBI (mTBI) | <20 minutes | <24 hours | GCS >13+ |
| Moderate TBI | >20 minutes, but <6 hours | | GCS 9-12 |
| Severe TBI | >6 hours | | GCS <8 |

For a brain injury to be classified as mTBI, the following conditions must be observed: (1) the length of consciousness is less than 20 minutes and amnesia is 24 hours or less, and (2) a GCS score of 13+.

mTBI is estimated to occur in 750,000 of over 2 million cases of TBI annually in the United States alone (see Anonymous, *Injury Fact Book*, National Center for Injury Prevention and Control: Atlanta, 2002). Based on statistics gathered by the National Center for Injury Prevention Center (NCIPC) at the Center for Disease Control (CDC), mTBIs are most commonly suffered from sports-related injuries, which account for approximately 300,000 injuries annually. The high incidence of mTBI among athletes has raised concern in professional sports organizations. For example, the National Hockey League supports an ongoing concussion study. Age groups most at risk are 15-24 and 75+ years of age. Males are twice as likely to suffer from mTBI as are females. Total costs attributable to mTBI exceed $17 billion annually.

The fundamental dilemma with mTBI lies in the fact that a practical, easy-to-administer diagnostic tool is not yet available. As a result, mTBI is commonly under-, or misdiagnosed, resulting in potential long-term consequences for patients. The present invention is designed to address this specific need.

As was mentioned above, in the United States, approximately 750,000 mild traumatic brain injuries (mTBI) occur every year. Mild traumatic brain injuries remain a serious public health and socioeconomic problem, resulting in long-term disability and death from secondary complications when not properly diagnosed (see Cantu, R. C., *Second-impact syndrome. Clinics in Sports Medicine*, 17(1):37-44, 1998, Cantu, R. C. and R. Voy, *Second-impact syndrome—a risk in any contact sport*, Physician and Sports Medicine. 23(6):27, 1995, and Kelly, J. P., J. S. Nichols, C. M. Filley, K. O. Lillehei, D. Rubinstein, and B. K. Kleinschmidt-DeMasters, *Concussion in sports, Guidelines for the prevention of catastrophic outcome*, JAMA).

Diagnosing mTBI is difficult even in the best setting. The signs and symptoms of mTBI are often very subtle and difficult to detect. Undiagnosed or under-diagnosed mTBI leads to poor clinical management and can often cause cognitive deficits, psychosocial problems, and secondary complications such as depression. See Englander, J., K Hall, T. Stimpson, and S. Chaffin, *Mild traumatic brain injury in an insured population: subjective complaints and return to employment*, Brain Tnj. 6(2):161-6., 1992, Farm, J. R., W. J. Katon, J. M. Uomoto, and P. C. Esselman, *Psychiatric disorders and functional disability in outpatients with traumatic brain injuries*, Am J Psychiatry. 152(10):1493-9., 1995, Gomez-Hernandez, R., J. B. Max, T. Kosier, S. Paradiso, and R. G. Robinson, *Social impairment and depression after traumatic brain injury*, Arch Phys Med Rehabil. 78(12):1321-6., 1997, Gronwall, D., *Cumulative and persisting effects of concussion on attention and cognition*, in Mild Head Injury, H. S. Levin, Eisenberg, Howard M., Editor, Oxford University Press; New York p. 153-162, 1989, Gronwall, D., *Performance changes during recovery from closed head injury*, Proc Aust Assoc Neurol. 13:143-7, 1976, Gronwall, D. and P. Wrightson, *Delayed recovery of intellectual function after minor head injury*, Lancet 2(7881):605-9., 1974, Gronwall, D. and P. Wrightson, *Memory and information processing capacity after closed head injury*, J Neurol Neurosurg Psychiatry. 44(10):889-95., 1981, Jorge, R. E., R. G. Robinson, S. V. Arndt, A. W. Forrester, F. Geisler, and S. E. Starkstein, *Comparison between acute-and delayed-onset depression following traumatic brain injury*, J Neuropsychiatry Clin Neurosci. 5(1):43-9., 1993, Stambrook, M., A. D. Moore, L. C. Peters, C. Deviaene, and G. A. Hawryluk, *Effects of mild, moderate and severe closed head injury on long-term vocational status*, Brain Tnj. 4(2):183-90., 1990, and van der Naalt, J., A. H. van Zomeren, W. J. Sluiter, and J. M. Minderhoud, *One year outcome in mild to moderate head injury: the predictive value of acute injury characteristics related to complaints and return to work*, J Neurol Neurosurg Psychiatry. 66(2):207-13., 1999. In addition, many cases mTBI are overshadowed by other injuries or by the events surrounding the injury, further confounding accurate diagnoses.

Mild cognitive decline that results from mTBI or degenerative diseases is often very subtle and difficult to detect. Frequently mTBI is overshadowed by other injuries or by the events surrounding the injury. The need for rapid and simple diagnostic testing for early detection is immense. The standard for evaluating possible cognitive deficits is neuropsychological testing. However, neuropsychological testing requires a quiet room void of distractions and the presence of trained personnel to administer, score, and interpret the measures. In addition, these tests may require several hours to perform. In many situations such as sideline assessment of a concussion in sports, these requirements make standard neuropsychological testing impractical.

The lack of diagnostic aids is especially apparent in athletic settings and can lead to repetitive injuries in children and young adults. For sports assessment of mTBI, length of test, ease-of-administration, and immersiveness are the top three criteria for a useable solution. The available approaches have not produced solutions that have all of these attributes.

For example, there are a number of known developmental efforts under way that are directed toward producing a neuropsychological assessment tool. Most of these solutions are software-based and aim to assess the cognitive functioning or impairment of the brain. For example, Neuroscience Solutions uses proprietary technology, sublicensed from Scientific Learning Corporation, based on established principles of "brain plasticity" to address neuropsychological disorders. NuCog is a cognitive assessment tool, developed by researchers in Australia, and is only available for limited use in research and clinical settings.

Of the 2 million traumatic brain injuries per year, [121 eighty percent are classified as "mild" (see Anonymous, *Injury Fact Book*, 2002, National Center for Injury Prevention and Control: Atlanta.). A substantial number of these patients experience initial objective neuropsychological difficulties involving memory, attention, and executive functioning. See Gronwall, D. and P. Wrightson, *Delayed recovery of intellectual function after minor head injury*. Lancet, 1974.2(788 1): p. 605-9, Dikmen, S., A. McLean, and N. Temkin, *Neuropsychological and psychosocial consequences of minor head injury*, J Neurol Neurosurg Psychiatry, 1986. 49(11): p. 1227-32, Dikmen, S. and J. E. Machamer, *Neurobehavioral outcomes and their determinants. Journal of Head Trauma Rehabilitation,* 1995. 10(1): p. 74-86, Hinton-Bayre, A. D., et al., *Concussion in contact sports: reliable change indices of impairment and recovery*. J Clin Exp Neuropsychol, 1999. 2 1(1): p. 70-86, Macciocchi, S. N., et al., *Neuropsychological functioning and recovery after mild head injury in collegiate athletes*. Neurosurgery, 1996. 39(3): p. 510-4, Ponsford, J., et al., *Factors influencing outcome following mild traumatic brain injury in adults*. Journal of the International Neuropsychological Society, 2000. 6(5): p. 568-79, and Levin, H. S., et al., *Neurobehavioral outcome following minor head injury: a three-center study*. J Neurosurg, 1987. 66(2): p. 234-43.

A significant subset of patients is left with persistent subjective cognitive complaints that disrupt their social relationships and their ability to resume leisure and work related activities (See van der Naalt, J., *Prediction of outcome in mild to moderate head injury: a review. Journal of Clinical &Experimental Neuropsychology,* 2001. 23(6): p. 837-51). The importance of the morbidity (i.e., prolonged cognitive deficits, affective and personality changes) and mortality (i.e., second impact syndrome) produced by mTBI has become increasingly appreciated. See Cantu, R. C. and F. O. Mueller, *Catastrophic football injuries:* 1977-1998. Neurosurgery, 2000.47(3): p. 673-5; discussion 675-7, Cantu, R. C., *Head and spine injuries in youth sports*. Clinics in Sports Medicine, 1995. 14(3): p. 517-32, Cantu, R. C., *Second-impact syndrome*. Clinics in Sports Medicine, 1998. 17(1): p. 37-44, Erlanger, D. M., et al., *Neuropsychology of sports-related head injury: Dementia Pugilistica to Post Concussion Syndrome*. Clinical Neuropsychologist, 1999.13(2): p. 193-209, and Kelly, J. P., et al., *Concussion in sports. Guidelines for the prevention of catastrophic outcome*. JAMA, 1991. 266(20): p. 2867-9.

There is good evidence that repetitive concussions result in long-term cognitive deficits and structural damage to the brain. See Cantu, R. C., *Second-impact syndrome*. Clinics in Sports Medicine, 1998. 17(1): p. 37-44, Kelly, J. P., et al., *Concussion in sports. Guidelines for the prevention of catastrophic outcome*. JAMA, 1991. 266(20): p. 2867-9, and Cantu, R. C. and R. Voy, *Second-impact syndrome—a risk in any contact sport*. Physician and Sports Medicine, 1995. 23(6): p. 27.

When a second concussion occurs prior to recovery from the first, rapid onset of cerebral edema and death can occur (See Cantu, R. C. and F. O. Mueller, *Catastrophic football injuries:* 1977-1998. Neurosurgery, 2000.47(3): p. 673-5; discussion 675-7, Cantu, R. C., *Head and spine injuries in youth sports*. Clinics in Sports Medicine, 1995. 14(3): p. 517-32, Cantu, R. C., *Second-impact syndrome*. Clinics in Sports Medicine, 1998. 17(1): p. 37-44, Erlanger, D. M., et al., *Neuropsychology of sports-related head injury: Dementia Pugilistica to Post Concussion Syndrome*. Clinical Neuropsychologist, 1999. 13(2): p. 193-209, and Kelly, J. P., et al., *Concussion in sports. Guidelines for the prevention of catastrophic outcome*. JAMA, 1991. 266(20): p. 2867-9), particularly for athletes prematurely returning to play.

In addition to these young adult populations, traumatic brain injury peaks in the aged population (See Frankowski, R. F., J. F. Annegers, and S. Whitman, *Part 1: The descriptive epidemiology of head trauma in the United States*. In: D. P. Becker, I T Povlishock (Eds.). Central Nervous System Trauma Status Report, 1985). With the escalating aging of the population, it has become imperative to develop efficient and accurate methods to diagnose mTBI in older adults. Approximately 21% of the U.S. population is older than age 55, and this will increase to 30% by the year 2025 (See Commerce, U.S.D.o., *Statistical Abstract of the United States 1997*. 1997, U.S. Department of Commerce, Bureau of the Census). The "oldest-old" (i.e. persons ^85 years) are increasing at the fastest rate.

Early detection of mTBI is critical to patient education and treatment and could potentially prevent secondary complications of depression and anxiety. Depression is a common secondary complication of mTBI. See Fenton, G., et al., *The postconcussional syndrome: social antecedents and psychological sequelae*. British Journal of Psychiatry, 1993. 162: p. 493-7, Mathias, J. L. and J. L. Coats, *Emotional and cognitive sequelae to mild traumatic brain injury*. Journal of Clinical & Experimental Neuropsychology, 1999. 21(2): p. 200-15, Schoenhuber, R. and M. Gentilini, *Anxiety and depression after mild head injury: a case control study*. Journal of Neurology, Neurosurgery & Psychiatry, 1988. 51(5): p. 722-4, Rutherford, W. H., J. D. Merrett, and J. R. McDonald, *Symptoms at one year following concussion from minor head injuries*. Injury, 1979. 10(3): p. 225-30, Levin, H. S., et al., *The neurobehavioural rating scale: assessment of the behavioural sequelae of head injury by the clinician*. Journal of Neurology, Neurosurgery & Psychiatry, 1987. 50(2): p. 183-93, and Levin, H. S., F. C. Goldstein, and E. J. MacKenzie, *Depression as a secondary condition following mild and moderate traumatic brain injury*. Seminars in Clinical Neuropsychiatry, 1997(2): p. 207-215.

Mittenberg and colleagues compared the effectiveness of standard hospital treatment and discharge instructions versus education concerning the symptoms and their management in mTBI patients. See Mittenberg, W., et al., *Cognitive-behavioral prevention of postconcussion syndrome. Archives of Clinical Neuropsychology*, 1996: p. 139-145. At six months postinjury, 28% percent of patients who received standard treatment met ICD-IO criteria for post-concussion syndrome, compared to only 11% of the preventative treatment group. Patients in the preventative group also reported significantly shorter overall symptom duration, fewer symptoms, fewer symptomatic days in the previous week, and lower symptom severity levels. One implication of this research is that early detection could lead to interventions to mitigate the morbidity associated with mTBI.

The diagnosis of mTBI is very challenging. This difficulty is largely a result of the continuing debate over the clinical definition of concussion. Most physicians agree on the physical signs and symptoms of a moderate and severe TBI (measured by the Glasgow Coma Scale (GCS) score; severe =3-8 and moderate=9-12), which are characterized by alterations in the level of consciousness. [36j However, patients with a mild TBI (GCS 13-15) by definition have almost no mental status changes profound enough to change their GCS score, and fewer than 10% result in an initial loss of consciousness. See Cantu, R. C., *Head injuries in sport*. British Journal of Sports Medicine, 1996. 30(4): p. 289-96, and Cantu, R. C., *Reflections on head injuries in sport and the concussion controversy. Clinical Journal of Sport Medicine*, 1997. 7(2): p. 83-4. Many of these patients do not initially seek medical attention or are under-diagnosed by the medical community, making the determination of true incidence impossible. Even when the diagnosis is suspected, patients are not being hospitalized for mTBI as often as in the past, indicating the need for greater surveillance and diagnosis of these cases in the emergency room and outpatient primary care facilities. See Thurman, D. and J. Guerrero, *Trends in hospitalization associated with traumatic brain injury. [comment]*. JAMA, 1999.282(10): p. 954-7.

The understanding of mTBI is further complicated by a lack of biomechanical understanding of the forces and deformations that lead to mild cognitive deficits. Although mechanical tolerances have been proposed for moderate and severe TBI, determination of thresholds for mTBI is complicated by poor patient recounts and delayed or inaccurate clinical diagnoses. See Lighthall, J. W., J. W. Melvin, and K. Ueno, *Toward a biomechanical criterion for functional brain injury*. Society of Automotive Engineers, Inc., 1989, and Margulies, S. S. and L. E. Thibault, *A proposed tolerance criterion for diffuse axonal injury in man*. Journal of Biomechanics, 1992. 25(8): p. 917-23. Early and reliable diagnosis of mTBI may not only assist the patient with rehabilitation and improved outcome, but it will also provide a tool to correlate the acute response to a mild insult with the mechanical circumstances of the injury.

Neuropsychological testing has proven useful in detecting the often subtle changes resulting from mTBI. See Dikmen, S., A. McLean, and N. Temkin, *Neuropsychological and psychosocial consequences of minor head injury*. J Neurol Neurosurg Psychiatry, 1986. 49(11): p. 1227-32, Hinton-Bayre, A. D., et al., *Concussion in contact sports: reliable change indices of impairment and recovery*. J Clin Exp Neuropsychol, 1999. 2 1(1): p. 70-86, Levin, H. S., et al., *Neurobehavioral outcome following minor head injury: a three-center study*. J Neurosurg, 1987. 66(2): p. 234-43, and Leininger, B. E., et al., *Neuropsychological deficits in symptomatic minor head injury patients after concussion and mild concussion*. J Neurol Neurosurg Psychiatry, 1990. 53(4): p. 293-6.

Table 3 shows results of representative studies conducted in the United States that have prospectively recruited patients with mTBI as opposed to retrospectively recruiting those patients who have complaints and thus introducing a selection bias. The results of these studies indicate cognitive impairments in the initial days that can be detected by formal neuropsychological testing.

TABLE 3

| Authors/Cognitive Outcome Measures | Findings |
|---|---|
| Barth et al., 1983/Wechsler Adult Intelligence Scale-R or Wechsler Intelligence Scale for Children-R, Halstead-Reitan Neuropsychological Test Battery, Wide Range Achievement Test, Wechsler Memory Scale | At 3 months postinjury, 44 pts (57%) had mild-severe impairments on Haistead-Reitan. |
| Dikmen et al., 1986/Haistead-Reitan Neuropsychological Test Battery, Wechsler Memory Scale, Selective Reminding Test | Pts significantly poorer in concentration and delayed verbal memory. |

TABLE 3-continued

| Authors/Cognitive Outcome Measures | Findings |
|---|---|
| Goldstein et al., 2000/California Verbal Learning Test, Continuous Recognition Memory, Controlled Oral Word Association, Trailmaking, Digit Span, Visual Naming, Wisconsin Card Sorting Test. | Mild TBI pts. 50 years and older exhibited performance, comparable to normal controls, on most measures within 2 months postinjury. Word fluency under timed conditions, however, was selectively impaired. |
| Hugenholtz et al., 1988/Simple Reaction Time (PT): Press response key with dominant hand to a single stimulus (e.g., circle); Choice RT: Press response key with dominant hand to a target stimulus (e.g., white circle), and respond with non-dominant hand for other shapes (e.g. white square, white triangle); Complex: Press response key with dominant hand to a target stimulus (e.g., white circle with horizontal lines) and respond with non-dominant hand for other shapes, colors, and line orientations (e.g., white circle with vertical lines, blue circle with horizontal lines) | 1. Within 3 days postinjury and up to 3 months postinjury, no significant differences between pts and controls on Simple RI task<br>2. Up to 17 days postinjury, pts significantly slower than controls on Easy Choice RI task but not at 1 and 3 months postinjury<br>3. Within 3 days postinjury and up to 1 month postmjury, pts significantly slower than controls on Complex Choice RI task but not at 3 months postinjury |
| Levin et al., 1987/Digit Span, Memory for animal names (Mattis-Kovner), Benton Visual Retention Test, Digit Symbol, Paced Auditory Serial Addition Task | 1. At 1 week postinjury, pts had significantly impaired attention, memory, and visuomotor and information processing speed (76%-87% of 57 pts below control mean performance in each domain)<br>2. At 1 month postinjury, no significant differences between pts and controls in Galveston and the Bronx; Pts in San Diego exhibited recovery of memory but continuing difficulties with attention and visuomotor and information processing speed<br>3. At 3 months postinjury, pts at all 3 centers were not significantly different from controls, except digit span which was lower in San Diego pts relative to controls |
| McAllister et al., 1999/Trail Making, Controlled Oral Word Fluency Test, Continuous Performance Test, Stroop Color Word Test, California Verbal Learning Test, Facial Memory, Working Memory Test | 1. At 1 to 5 weeks postinjury, pts significantly slower in simple reaction time and reaction time under distraction.<br>2. No significant differences in word fluency, verbal and visual memory, or other measures of attention |
| Rimel et al., 1981/Wechsler Scales of Intelligence, Wechsler Memory Scale, Halstead-Reitan Neuropsychological Test Battery, Wide Range Achievement Test | 1. At 3 months postinjury, pts exhibited mild deficits involving attention-concentration and problem-solving<br>2. No significant impairments, based on published norms, in overall intellectual functioning and academic achievement |

However, the practicality of neuropsychological testing is limited, as it requires a quiet room, few distractions, and trained personnel to administer, score, and interpret the measures. These conditions are rarely available when most mTBI patients need to be evaluated in the initial days postinjury. In addition, these tests may require several hours to perform. In many situations, such as sideline assessment of concussion or in a busy emergency department, these requirements make standard neuropsychological testing impractical. Moreover, testing in doctors' offices and other non-specialized medical facilities is currently limited due to the specialized training and time required to administer these tests. A concise, portable test that maintains sensitivity for mTBI would allow better management of these patients and provide marked improvement in disease surveillance and outcomes.

Papers have been published relating to virtual reality and neuroscience. Exemplary papers include "VIRTUAL REALITY IN NEUROSCIENCE: A SURVEY", Giuseppe Riva, *Virtual Environments in Clinical Psychology and Neuroscience*, Ios Press: Amsterdam, Netherlands, "Virtual Reality and Cognitive Assessment and Rehabilitation: The State of the Art", Albert A. Rizzo and J. Galen Buckwalter, Ios Press: Amsterdam, Netherlands, and "Virtual Environments in Neuropsychological Assessment and Rehabilitation", F. D. Rose, E. A. Attree and B. M. Brooks, Ios Press: Amsterdam, Netherlands, all of which generally discuss the use of virtual reality in neuroscience, However, no systems are discussed in these papers that provide for a portable audio-visually immersive evaluation tool.

Thus, although computer-based neuropsychological tests for mTBI evaluation are available, none of these systems provide an immersive, portable, site-of-injury format The need for rapid, simple and convenient diagnostic testing for early detection of mTBI is immense.

SUMMARY OF THE INVENTION

The present invention comprises cognitive assessment systems and methods that provide an integrated solution for evaluating the presence or absence of cognitive impairment. The present invention is used to test cognitive functions of an individual including information processing speed, working memory, work list learning and recall, along with variations of these tasks. Testing using the present invention may be completed in real time, typically in less than 15 minutes.

Embodiments of the present invention provide for non-immersive and immersive systems and methods. The present invention implements cognitive assessment systems and method for testing cognitive impairment of an individual.

An exemplary non-immersive system is embodied in a portable computing device that comprises audio and video output devices, and a response selection device that allows the individual to make response selections responding to predefined neuropsychological tests presented to the individual. Software runs on the portable computing device that (1) presents the predefined neuropsychological tests to the individual, and (2) processes the response selections to evaluate cognitive functions of the individual to generate test results that are indicative of the presence or absence of cognitive impairment.

An exemplary immersive cognitive assessment system comprises a portable computing device, headgear with audio-visual immersion that is worn by an individual to be tested that includes audio and video output devices, and a response selection device coupled to the headgear that allows the individual to make response selections responding to predefined neuropsychological tests presented to the individual free of distractions from the environment Software runs on the portable computing device that (1) presents the predefined neuropsychological tests to the individual by way of the headgear mounted display, and (2) processes the response selections to evaluate cognitive functions of the individual to generate test results that are indicative of the presence or absence of cognitive impairment.

In either of the above embodiments, the portable computing device may include a database that stores pre-injury test data or baseline data (norms) for similar subjects that is used for comparison with the tests that are given to the individual.

In an exemplary non-immersive cognitive assessment method, predefined neuropsychological tests are presented to the individual. The individual makes response selections based upon what is presented in the tests. The response selections of the individual are immediately processed to evaluate cognitive functions of the individual and to generate test results that are indicative of the presence or absence of cognitive impairment.

In an exemplary immersive cognitive assessment method, the individual wears headgear, comprising audio and video output devices, that immerses the individual in an audio-visually immersive environment. The tests are performed and processed to generate test results that are indicative of the presence or absence of cognitive impairment.

BRIEF DESCRIPTION OF THE DRAWINGS

The various features and advantages of embodiments of the present invention may be more readily understood with reference to the following detailed description taken in conjunction with the accompanying drawings, wherein like reference numerals designate like structural elements, and in which:

FIG. 4 is a side view of a second embodiment of headgear that may be employed in the system shown in FIG. 1;

FIG. 5 is a side view of a third embodiment of headgear that may be employed in the system shown in FIG. 1;

FIG. 6 is a side view of a fourth embodiment of headgear that may be employed in the system shown in FIG. 1;

FIG. 8 is a flow chart that illustrates work flow performed in testing patients using the systems;

FIG. 9 illustrates an exemplary simple and complex choice reaction time test employed in the systems;

FIG. 10 illustrates an exemplary selective reminding memory test employed in the systems;

FIG. 11 is a flow diagram that illustrates an exemplary N-back test order;

FIG. 12 is an enlarged view that illustrates an exemplary N-back working memory test employed in the systems;

FIG. 13 illustrates an exemplary 1-back test;

FIG. 14 illustrates an exemplary 2-back test;

FIG. 15 is a flow diagram illustrating exemplary embodiments of immersive cognitive assessment methods in accordance with the principles of the present invention; and FIG. 16 is a flow diagram illustrating exemplary embodiments of non-immersive cognitive assessment methods in accordance with the principles of the present invention.

DETAILED DESCRIPTION

Figure 1:
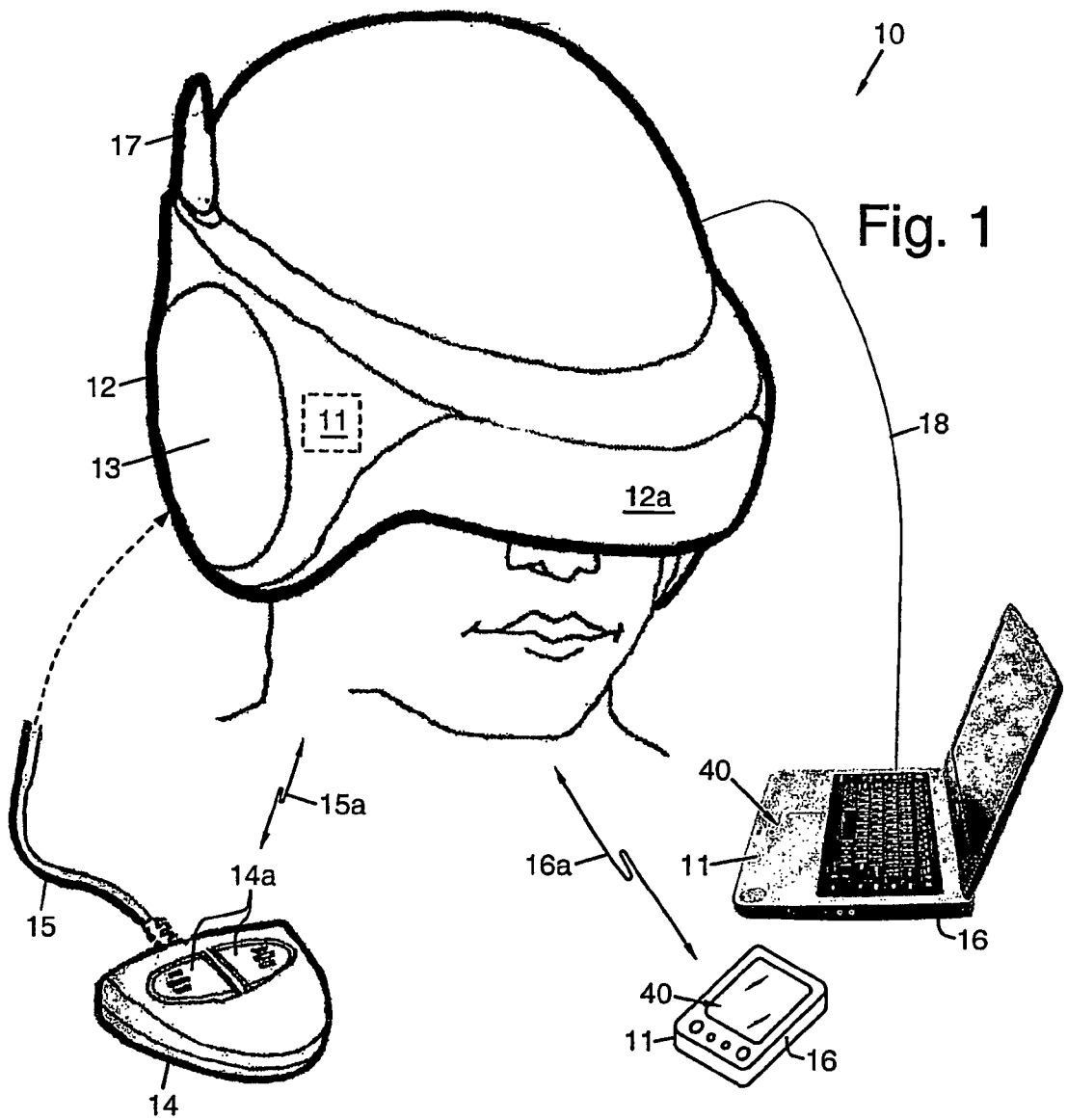
FIG. 1 illustrates exemplary embodiments of an immersive cognitive assessment tool or system in accordance with the principles of the present invention for evaluating the presence or absence of cognitive impairment of an individual.
Figure 2:
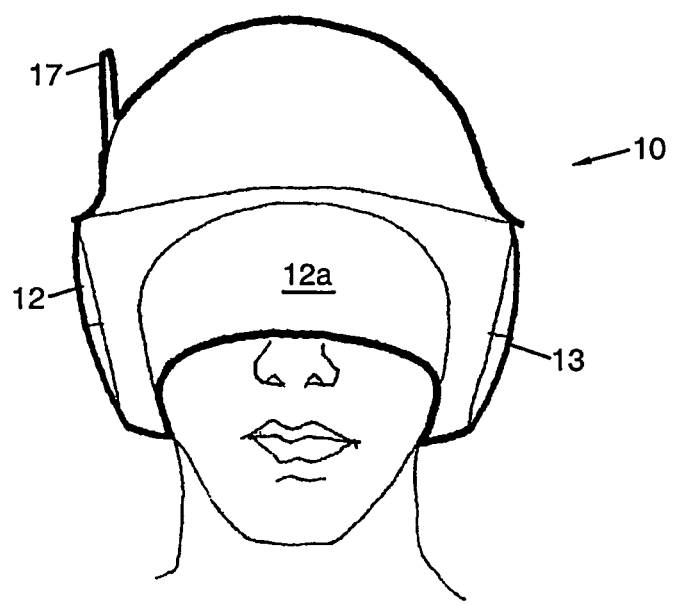
FIG. 2 is a front view of headgear employed in the system shown in FIG. 1.
Figure 3:
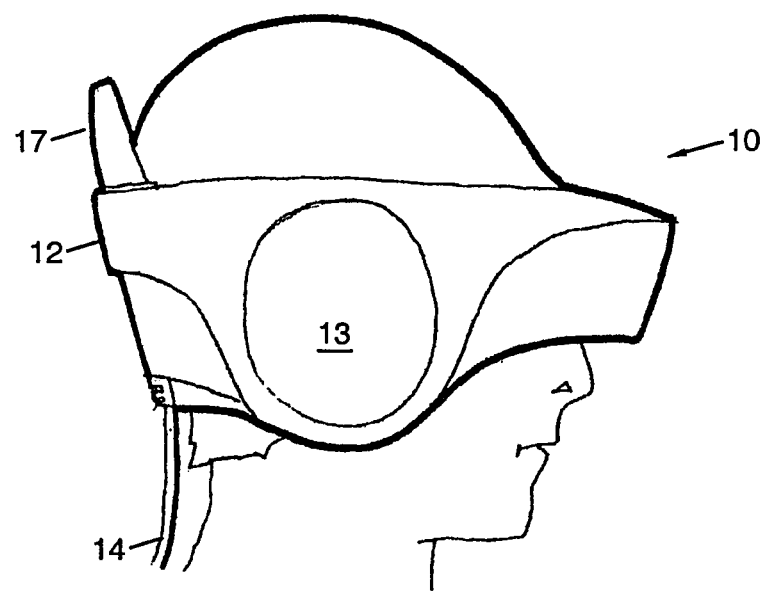
FIG. 3 is a side view of the headgear shown in FIG. 1.

Referring to FIG. 1, it illustrates exemplary embodiments of immersive cognitive assessment tools 10 or systems 10 in accordance with the principles of the present invention for diagnosing concussions and mild traumatic brain injury. FIGS. 2 and 3 show front and side views, respectively, of headgear 12 used in the exemplary immersive cognitive assessment tools 10 or systems 10 shown in FIG. 1.

The exemplary tool 10 or system 10 comprises a portable system 10 including a portable computing device 11, such as a portable computer 11 or a personal digital assistant (PDA), for example, and a software application 40 that runs on the portable computing device 11. The exemplary tool 10 or system 10 also comprises headgear 12 that is worn by an individual to be tested that totally immerses the individual within a test environment, The headgear 12 includes a display screen 12a and audio output device 13, such a headphones, for example. A response selection device 14 is coupled to the headgear 12. The response selection device 14 may comprises input buttons 14a or switches 14a of a mouse-like device, or may be selection buttons 14a on the portable computing device 11. Other embodiments of the portable computing device 11 may be housed within the headgear 12, for example (shown using a dashed box).

The portable computing device 11 (portable computer 11 or PDA 11) may include a wireless communication device 16 that allows it to wirelessly communicate with the headgear 12 using an antenna 17 in the headgear 12 and a wireless communication link 16a. The response selection device 14 may be coupled to the headgear 12 by way of a wired connection 15. Alternatively, the response selection device 14 may be a wireless device 14 that is coupled to the headgear 12 by way of a wireless connection 15a, such as is provided by a BLUETOOTH® radio data link, for example.

Figure 1A:
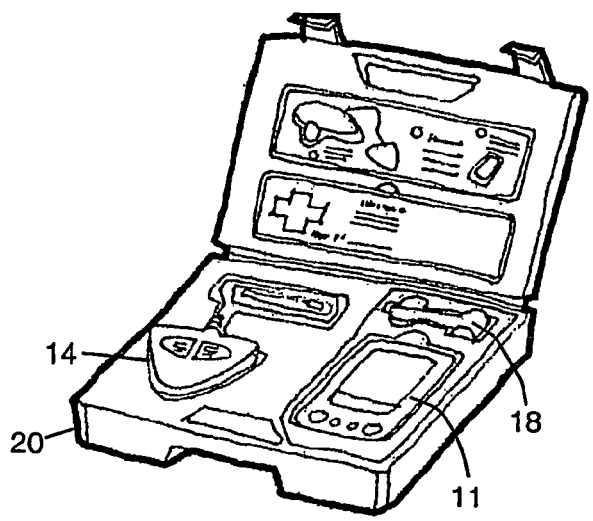
FIG. 1a illustrates an exemplary carrying case for storing components of the system shown in FIG. 1.

FIG. 1a illustrates an exemplary padded carrying case 20 for storing components of the system shown in FIG. 1. The padded carrying case 20 is configured to store the response selection device 14, a PDA 11 and a cable 22 for connecting the PDA 11 to the headgear 12. Again, it is to be understood that embodiments of the present invention may have the portable computing device 11 wired to or wirelessly coupled to the headgear 12. FIG. 1a illustrates the truly portable, field-useable, nature of the present invention.

FIGS. 4-6 show other exemplary embodiments of the headgear 12. FIG. 4 shows exemplary bicycle-style helmet headgear 12 including a connector jack 15b to which the response selection device 14 may be connected. FIG. 5 shows exemplary visor-style helmet headgear 12 also including a connector jack 15b. FIG. 6 shows an exemplary embodiment of visor-style helmet headgear 12 wherein the response selection device 14 is hard wired to the headgear 12. In addition, the headgear 12 may be in the form of a football helmet having a facemask comprising the display screen 12a.

A prototype of the immersive cognitive assessment tool 10 or system 10 was reduced-to-practice using off-the-shelf components shown in Table 4 to test the concept of the system 10 shown in FIG. 1. Specific hardware components were chosen that contribute to an immersive environment, are easy to use, and are comfortable to wear by subjects. These hardware components include BOSE® active noise reduction (ANR) aviation headphones 13, SONY® and OLYMPUS® visual display headgear 12 and display screen 12a, a user interface comprising the response selection device 14, and a DELL® LATITUDE® laptop computer 11 as the portable computing device 11.

TABLE 4

Components of the prototype system

| Component | Function | Manufacturer & Specification |
|---|---|---|
| Portable computer | Data storage and program interface | Dell Latitude C840 notebook computer with a Mobile Pentium ® processor (2.2 GHz, 512 MB RAM, 40 GB Hard Drive), 64 MB DDR video card, Windows ® XP Professional version 2002 (SP1) |
| Visual display | Visual immersion | Two versions: 1) Sony Glasstron & JO Display systems 2) 1 glasses |
| Noise reduction headphones | Audio immersion | Bose ® Aviation Headset X active noise reduction (ANR) headphones |
| Switches | Input Device | Two Jelly Bean ® switches connected to X - keys USB Switch Interface and programmed to respond to a 'Yes or 'No button |

The complete system 10 is comprised of a laptop computer, 11 input buttons 14a, and headgear 12 SONY® visor and BOSE® ANR headset), hard-wired together. The computer 11 and accessories fit into a padded case 20 for portability. The user holds the input buttons 14a and listens to instructions while sitting down. It is to be understood that the above-mentioned components of the system 10 may be housed as a single integrated and wireless unit.

An initial version of the software for the neuropsychological testing component (software 40) of the system 10 was developed following an extensive literature review relating to mTBI and consultation with practicing neuropsychologists. Three neuropsychological tests were chosen for inclusion in the system based on their practicality and sensitivity parameters which are outlined in Table 5. These tests include N-back working memory, simple and complex reaction time, and selective reminding.

TABLE 5

Neuropsychological tests programmed for the system

| Test | Measures | Time (mm) |
|---|---|---|
| N-Back Working Memory Task | Working memory with increase load | 5 |
| Simple and Complex Choice Reaction Time | Information processing speed | 5 |
| Working Memory | Memory | 5 |

Software 40 derived from the above three standard neuropsychology tests was created using Virtual Basic. These tests examine areas that are especially vulnerable to early mTBI including memory and speed of processing (See Buschke, H. and P. A. Fuld, *Evaluating storage, retention, and retrieval in disordered memory and learning*. Neurology, 1974. 24(11): p. 1019-25, Hugenholtz, H., et al., *How long does it take to recover from mild concussion?* Neurosurgery, 1988. 22: p. 853-858, and MacFlynn G., M. E. A., Fenton, G. W., Rutherford, W., *Measurement of reaction time following minor head injury*. Journal of Neurology and Neurosurgical Psychiatry, 1984).

Figure 7:
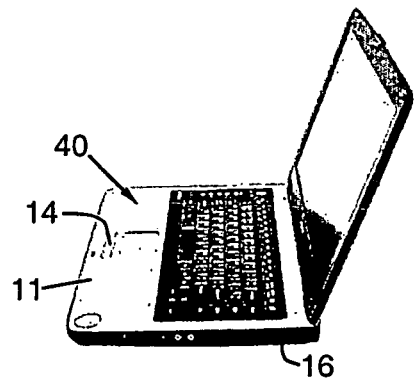
FIG. 7 illustrates an exemplary embodiment of a non-immersive cognitive assessment tool or system in accordance with the principles of the present invention.

FIG. 7 illustrates an exemplary embodiment of non-immersive cognitive assessment tools 10 or systems 10 in accordance with the principles of the present invention. The non-immersive cognitive assessment tools 10 or systems 10 may be used in testing individuals that may have Alzheimers disease, for example, or in cases where an immersive environment is not necessary.

An exemplary non-immersive system 10 is embodied in a portable computing device 11 that comprises video and audio output devices 12a, 13, and a response selection device 14 that allows the individual to make response selections responding to predefined neuropsychological tests presented to the individual. In this embodiment of the system 10, the video output device 12a is a display screen of the portable computing device 11 and the audio output device 13 is a speaker system of the portable computing device 11. The response selection device 14 may be built-in selection buttons or selected keys of the portable computing device 11. Software 40 runs on the portable computing device 11 that (1) presents the predefined neuropsychological tests to the individual, and (2) processes the response selections to evaluate cognitive functions of the individual to generate test results that are indicative of the presence or absence of cognitive impairment.

FIG. 8 is a flow chart that illustrates exemplary work flow 20 performed in testing using the systems 10. Introductory screening 21 is performed on subject. Then, a battery of tests/tasks (involving sequences of tests/tasks) are performed using the system 20. The tests include a simple and complex choice reaction time test 33, a selective reminding test 23, a series of N-Back tests 24, and a long term selective reminding test 25. FIGS. 9-14 illustrate details of the testing that is performed using the system 10.

FIG. 9 illustrates an exemplary simple and complex choice reaction time test 22 employed in the system 10. FIG. 10 illustrates an exemplary selective reminding memory test 23 employed in the system 10. FIG. 11 is a flow diagram that illustrates ordering of an exemplary N-back test 24. The N-back test 24 includes a first 0-back test 31, a first 1-back test 32, a first 2-back test 33, a second 0-back test 34, a second 1-back test 35, and a second 2-back test 35. FIG. 12 is an enlarged view that illustrates an exemplary N-back working memory test displayed on the display screen 12a of the system 10. FIG. 13 illustrates an exemplary 1-back test 32. FIG. 14 illustrates an exemplary 2-back test 33.

The N-Back working memory task 24 utilizes a non-verbal version in which subjects determine whether a particular stimulus appears in a specific location. The demands of the N-Back working memory task 24 are increased from a 0-load, a 1-load and a 2-load. The simple and complex choice reaction time task 22 requires the subject to focus on increasing dimensions of a stimulus before making a response. The simple and complex choice reaction time task 22 varies from an easy version (i.e., respond whenever you see a red circle) to a harder version (i.e., respond whenever you see a red circle with diagonal lines and ignore all other red circles or other colored circles with diagonal lines).

The hardware components and initial software have been tested together. Initial usability testing of the system 10 has been done with normal college age volunteer subjects in a controlled, artificially simulated noisy environment.

In the usability study, it was found that there was no difference in test results obtained using the present invention in a quiet room versus a simulated noisy environment. The advantage of total immersion allows the present invention to be used on-site, even in a noisy environment such as a sporting event. Therefore, the system has great potential for use as a side-line assessment tool for mTBI as well as application that require portability and ease-of-use.

The specific results from these tests are given below:

1. Objective evaluation of the system 10 in quiet and artificially induced noisy environments.

To test the ability of to create an effective immersive environment that is void of external visual and auditory distractions, normal healthy volunteer subjects (n=42) were recruited and randomly assigned to two groups. The headgear 12 was worn at all times in both groups. Group 1 completed neuropsychological tests using the system 10 in a quiet environment. This same group was then required to retake the test in an artificially induced external noisy environment (−0.75 decibels of fluctuating noise, equivalent to an average football game crowd). Group 2 took the same test in the noisy environment first, and then completed the second round of tests in the quiet environment. Between group comparisons (noisy to quiet group vs. quiet to noisy group) were made as well as individual changes between the 1st and 2nd tests (from noisy to quiet or quiet to noisy). The findings show that the quiet and noisy environments did not contribute to statistically significant differences (p>0.1) in participants' test scores or response times when taking the test.

2. Subjective usability survey.

After completing the two neuropsychological tests using the system 10, the volunteer subjects completed a post-task survey. The findings show that the subjects thought the system 10 blocked out visual and audio distractions. They also thought both the head-mounted display 12a and the ear muffs (headphones 13 were comfortable to wear. They strongly agreed that the buttons 14a of the response selection device 14 they interacted with were easy to use.

Data derived from the tests indicate that the system 10 provides an adequate immersive environment for neuropsychological testing even in an artificially produced noisy environment.

An embodiment of the portable computing device 11 may include a relatively large testing databank that is stored in a database 19. The databank stores pre-injury test data that is used for comparison with later tests. Alternatively, without pre-injury test data, tests are compared against norms or baseline data for similar subjects that may be stored in the database 19. The software 40 may include an algorithm that implements autoscoring to provide immediate scoring of test results. For the system 10 to be used as a screening tool, individual subjects are generally required to take the tests more than once. For example, for football players, prescreening neuropsychological testing is performed preseason and repeated if a head injury is suspected. The act of retaking the tests can alone improve the test scores. This improvement in scores from repeated testing is known as the "learning effect." It has been well-described in the literature for almost all available tests. One way to minimize this effect is to provide different questions or stimuli each time the test is taken. In this way, the learning effect is reduced, but not totally eliminated. The system 10 may also be modified to enlarge the question bank to provide five different versions of the tests.

Pre-injury history, epidemiological, and background information can affect the interpretation of neuropsychological test results. Because of this, it is desirable to gather pre-injury data against which future test data may be compared. Examples of baseline data include: history of head injury in the past, history of intracranial pathology, history of mental retardation, age, level of education, and the like. Incorporating the database 19 containing the databank in the system 10 that is accessible by the software 40 greatly enhances the portability of the system 10, make it less reliant on monitoring personnel, and permits generation of real-time score results. No known cognitive testing system provides this capability.

The software 40 grades the test results and measures differences in scores compared to baseline scores from the databank or from "normal" data. The software 40 may include the self-scoring algorithm that can grade and provide standard deviations from norms or from a subject's previous scores (i.e., data in the databank. The ability to immediately determine the score, and hence the degree of cognitive impairment, significantly enhances the usability and portability of the system 10.

The system 10 and software 40 provide for a method that allows subjects with possible preclinical Alzheimer's disease to be tested, providing an alternative method for early diagnosis. The system 10 is used to administer tests to a geriatric patient population to diagnose preclinical Alzheimer's disease.

Alzheimer's disease is a progressive neurodegenerative disorder that causes impaired thinking and behavior. Alzheimer's disease affects 4 million Americans, and is the most expensive condition to treat following heart disease and cancer. It is estimated that more than 14.3 million Americans will have Alzheimer's disease by the year 2050 (See Evans, D. A., H. H. Funkenstein, M. S. Albert, P. A. Scherr, N. R. Cook, M. J. Chown, L. E. Hebert, C. H. Hennekens, and J. O. Taylor, *Prevalence of Alzheimer's disease in a community population of older persons. Higher than previously reported. [comment]*. JAMA. 262(18):2551-6, 1989, and McNeil, C., Alzheimer's Disease: Unraveling the Mystery, NIB, National Institute on Aging. Bethesda, Md., 1997).

Although there is no cure at present for Alzheimer's disease, early detection of symptoms and slowing of the disease course via pharmacologic agents offer great promise. Early detection is the key to implementing new therapies and interventions. It has been found that the system 10 can detect early cognitive decline in patients with Alzheimer's disease. The system has been evaluated using geriatric patients who do not yet meet diagnostic criteria for Alzheimer's disease but who have evidence of mild cognitive impairment on neuropsychological measures.

The protocol entails contacting potential candidates and scheduling them for testing. Each subject completes both the screening and undergo standard pen and paper versions of the neuropsychological tests. Subjects are randomly assigned to take either the system test first or the standard tests. Results were statistically compared to determine the sensitivity of the system 10 as compared to standard pen and paper neuropsychological tests (Table 6).

TABLE 6

Neuropsychological battery for validation in Alzheimer's disease patients

| Test | Measures | Time (min) |
| --- | --- | --- |
| Paced Serial Addition Task | Information processing speed and working memory | 10 |
| Controlled Oral Word Association Test | Speeded measure: word list generation: sensitive to frontal lobe deficits | 5 |
| Trail Making | Set shifting under timed conditions | 10 |
| Selective Reminding Memory Test | Word list learning and recall | 10 |
| Wisconsin Card Sorting Test | Hypothesis generation and response shifting | 10 |
| N-back Working Memory Task | Working memory with increase load | 5 |
| Simple and Complex Choice Reaction Time | Information processing speed | 5 |

Tests were performed to validate the use of the system 10 in patients with known cognitive impairments from a prior severe head injury. The system 10 was tested to determine the sensitivity of the system 10 for detecting cognitive deficits in head injured patients. Use of a population of patients that are currently known to have cognitive deficits from TBI increases the power to detect difference between the system 10 and the standard neuropsychological tests employed. Only patients capable of undergoing testing with both the head mounted display 12a and the pen and paper versions were enrolled. Testing in this population allowed verification that the system 10 is able to clearly pick up less subtle cognitive deficits and compare crude categories of severity with the pen and paper version of the neuropsychological tests.

For the purposes of completeness, FIGS. 15 and 16 are flow diagrams illustrating exemplary embodiments of immersive and non-immersive cognitive assessment methods 50, 60, respectively, in accordance with the principles of the present invention.

FIG. 15 is a flow diagram illustrating exemplary embodiments of the immersive cognitive assessment methods 50. An exemplary immersive method 50 for assessing cognitive capabilities of an individual is implemented as follows.

An individual wears 51 headgear, comprising audio and video output devices, that immerses the individual in an audio-vidually immersive environment. Predefined neuropsychological tests are presented 52 to the individual using the headgear. The individual makes 53 response selections based upon what is presented in the tests. The response selections of the individual are processed 54 (preferably immediately) to evaluate cognitive functions of the individual to generate test results that are indicative of the presence or absence of cognitive impairment. An autoscoring software algorithm that is part of the software may be used to provide substantially immediate test results.

FIG. 16 is a flow diagram illustrating exemplary embodiments of non-immersive cognitive assessment methods 60. An exemplary non-immersive method 60 for assessing cognitive capabilities of an individual is implemented is implemented as follows.

Predefined neuropsychological tests are presented 61 to an individual. The individual makes 53 response selections based upon what is presented in the tests. The response selections of the individual are processed 54 (preferably immediately) to evaluate cognitive functions of the individual to generate test results that are indicative of the presence or absence of cognitive impairment. An autoscoring software algorithm that is part of the software may be used to provide substantially immediate test results.

In summary, the present invention provides for portable systems 10 and methods 50, 60 that implement fast, easy to administer, and sensitive testing of cognitive impairment of individuals. The applications for this technology are tremendous and range from sideline assessment of concussion and emergency room and field evaluation of TBI. Additional cognitive assessment applications, such as early assessment of Alzheimer's disease, may also benefit from using the systems 10 and methods 50, 60.

Neuropsychological tests were generated that take five minutes each to complete, for a total testing time of approximately 15 minutes for three sets of tests. The chosen tests are known to be sensitive for detecting mild concussion in a traditional environment. The use of abbreviated but sensitive neuropsychological tests provide for a highly-useful portable system 10 for diagnosing mTBI.

Thus, systems and methods for testing cognitive impairment of individuals have been disclosed. It is to be understood that the above-described embodiments are merely illustrative of some of the many specific embodiments that represent applications of the principles of the present invention. Clearly, numerous and other arrangements can be readily devised by those skilled in the art without departing from the scope of the invention.

What is claimed is:

1. A portable, field-usable immersive cognitive assessment system for testing a cognitive state of an individual by delivery of computer-generated neuropsychological testing, comprising:

portable headgear, comprising an audio output device and a video output device integrated into the headgear, configured to be worn by the individual to create an environment effective to minimize external audio and visual distractions during the testing, the audio output device providing audible sounds to the individual and including a noise reduction circuit, the video output device comprising a computer display screen mounted to the headgear effective to substantially cover the entire field of view of the individual when worn for administration of neuropsychological testing;

a response selection device that is configured to receive response selections input by the individual in response to a presented neuropsychological test; and a portable computing device coupled to the headgear and the response selection device and including software that (a) presents a battery of predefined time-limited neuropsychological tests, each test requiring a predetermined response based on what is presented in the test to the individual via at least one of the audio and video output devices of the headgear, (b) receives response selections input by the individual via the response selection device in response to each test of the battery of presented neuropsychological tests, (c) determines a score from each test of the battery of presented neuropsychological tests, and (d) presents the score of the presented neuropsychological tests to a test administrator in real-time after administration of the battery of tests as a measure of a degree of cognitive impairment, wherein the battery of predefined time-limited neuropsychological tests include questions selected from a question bank, the question bank being configured to be modified or enlarged to provide different versions of the predefined time-limited neuropsychological tests.

2. The system recited in claim 1, wherein the predefined neuropsychological test comprises at least one cognitive function test that evaluates at least one of reaction time, processing speed, and working memory.

3. The system recited in claim 1, wherein a testing time required for the computing device to present the battery of time-limited neuropsychological tests to the individual and the response selection device to receive response selections input by the individual is 15 minutes or less.

4. The system recited in claim 1, wherein the battery of time-limited predefined neuropsychological tests comprises three tests that can be completed in approximately 15 minutes or less.

5. The system recited in claim 1, wherein the cognitive impairment includes cognitive impairment caused by mild traumatic brain injury to the individual.

6. The system recited in claim 1, wherein the cognitive impairment includes cognitive impairment caused by a neurodegenerative disorder.

7. The system recited in claim 1, wherein the cognitive impairment includes cognitive impairment caused by Alzheimer's disease.

8. The system recited in claim 1, wherein the computing device comprises the response selection device.

9. The system recited in claim 1, wherein the computing device is wirelessly coupled to the headgear.

10. The system recited in claim 1, wherein the response selection device is wired to the computing device.

11. The system recited in claim 1, wherein the computing device comprises software comprising an autoscoring algorithm that generates the score.

12. The system recited in claim 1, further comprising a database coupled to the computing device for storing a databank of comparison data against which a particular test of an individual is compared.

13. The system recited in claim 12, wherein the databank of comparison data comprises pre-injury test data that is used for comparison with later tests.

14. The system recited in claim 13, wherein the pre-injury test data includes data selected from the group comprising: history of head injury in the past, history of intracranial pathology, history of mental retardation, age, level of education.

15. The system of claim 13, wherein the pre-injury test data includes pre-season neuropsychological testing.

16. The system recited in claim 12, wherein the databank of comparison data comprises baseline test data for similar subjects that is used for comparison with a test of a particular individual.

17. The system recited in claim 12, wherein the databank of comparison data is loaded onto the system prior to use, whereby real-time score results are provided from administration of a neuropsychological test compared to said comparison data.

18. The system recited in claim 12, wherein the computing device software grades test results and measures differences in scores of a particular test of an individual against the comparison data.

19. The system recited in claim 18, wherein the differences in scores are relative to baseline scores.

20. The system recited in claim 18, wherein the differences in scores are relative to data of other individuals.

21. The system recited in claim 1, wherein a test in the battery of tests is selected from the group comprising: a choice reaction time test, a selective reminding test, a series of N-back tests, and a long term selective reminding test.

22. A method for assessing cognitive capabilities of an individual by delivery of a battery of computer-generated neuropsychological tests, comprising the steps of:
providing a portable, field-usable computing device for delivering a battery of time-limited computer-generated neuropsychological tests, each of which requires a predetermined response based on what is presented in a test to the individual by way of audible sounds, visual information, or both, and receiving responses to each test of the battery of tests by way of a response selection device actuated by the individual and that is coupled to the computing device;
placing portable headgear on the individual in a field environment and administering the neuropsychological test within an environment created by the headgear that is effective to minimize external audio and visual distractions during the test, the portable headgear comprising an audio output device and a video output device coupled to the portable computing device, the audio output device providing audible sounds to the individual and including a noise reduction circuit, the video output device comprising a computer display screen mounted to the headgear effective to substantially cover the entire field of view of the individual;
presenting a battery of time-limited predefined computer-generated neuropsychological tests to the individual via the headgear during a predetermined time period, the battery of predefined time-limited neuropsychological tests including questions selected from a question bank, the question bank being configured to be modified or enlarged to provide different versions of the predefined time-limited neuropsychological tests;
receiving response selections input by the individual via the response selection device in response to each one of the battery of presented neuropsychological tests;
processing via the computing device the response selections of the individual to determine a score from each of the presented neuropsychological tests that scores the cognitive functions of the individual and generates test results that are indicative of a cognitive state of the individual in real-time; and
presenting the test results to a test administrator in real-time after administration of the battery of tests as a measure of a degree of cognitive impairment.

23. The method recited in claim 22, wherein the predefined neuropsychological test comprises at least one cognitive function test that evaluates at least one of reaction time, processing speed, and working memory.

24. The method recited in claim 22, wherein the battery of time-limited predefined neuropsychological tests comprises a plurality of tests that can be presented during a predetermined time period of 15 minutes or less.

25. The method recited in claim 22, wherein the cognitive impairment includes cognitive impairment caused by mild traumatic brain injury to the individual.

26. The method recited in claim 22, wherein the cognitive impairment includes cognitive impairment caused by a neurodegenerative disorder.

27. The method recited in claim 22, wherein the cognitive impairment includes cognitive impairment caused by Alzheimer's disease.

28. The method recited in claim 22, further comprising a database coupled to the computing device for storing a databank of comparison data against which a particular test of an individual is compared.

29. The method recited in claim 28, wherein the databank of comparison data comprises pre-injury test data that is used for comparison with later tests.

30. The method recited in claim 29, wherein the pre-injury test data includes data selected from the group comprising: history of head injury in the past, history of intracranial pathology, history of mental retardation, age, level of education.

31. The method recited claim 28, wherein the individual is an athlete that is provided with pre-season neuropsychological testing preseason and where a neuropsychological test is repeated with the individual if a head injury is suspected.

32. The method recited in claim 28, wherein the databank of comparison data comprises baseline test data for similar subjects that is used for comparison with a test of a particular individual.

33. The method recited in claim 28, wherein the databank of comparison data is loaded onto the device prior to use, whereby real-time score results are provided from administration of a neuropsychological test compared to said comparison data.

34. The method recited in claim 28, wherein the computing device software grades test results and measures differences in scores of a particular test of an individual against the comparison data.

35. The method recited in claim 34, wherein the differences in scores are relative to baseline scores.

36. The method recited in claim 34, wherein the differences in scores are relative to data of other individuals.

37. The method recited in claim 22, wherein a test in the battery of tests selected from the group comprising: a choice reaction time test, a selective reminding test, a series of N-back tests, and a long term selective reminding test.

* * * * *